United States Patent [19]
Wang

[11] Patent Number: 5,128,436
[45] Date of Patent: Jul. 7, 1992

[54] CYCLIC POLYHYDROXY POLYETHER OLIGOMERS HAVING SPIRODILACTAM UNITS

[75] Inventor: Pen C. Wang, Houston, Tex.

[73] Assignee: Shell Oil Company, Houston, Tex.

[21] Appl. No.: 747,068

[22] Filed: Aug. 19, 1991

[51] Int. Cl.⁵ .................... C08G 52/26; C08G 69/14
[52] U.S. Cl. ...................... 528/96; 540/466; 540/468
[58] Field of Search ............ 528/96; 540/466, 468

[56] References Cited

U.S. PATENT DOCUMENTS

| | | | |
|---|---|---|---|
| 4,672,102 | 6/1987 | Silvis et al. | 528/96 |
| 4,888,408 | 12/1989 | Wang | 528/96 |
| 4,889,907 | 12/1989 | Wang | 528/96 |
| 4,933,423 | 6/1990 | Wang | 528/96 |
| 4,939,227 | 7/1990 | Wang | 528/96 |
| 5,001,213 | 3/1991 | Wang | 528/96 |

Primary Examiner—John C. Bleutge
Assistant Examiner—Frederick Krass

[57] ABSTRACT

Novel cyclic oligomers contain moieties of 2-hydroxyl-1,3-propylene alternating with moieties of 1,6-di(oxyphenyl) 1,6-diaza [4.4] spirodilactam and, optionally, di(oxyphenyl) compound. The oligomers are thermoplastic resin of the phenoxy resin type.

25 Claims, No Drawings

CYCLIC POLYHYDROXY POLYETHER OLIGOMERS HAVING SPIRODILACTAM UNITS

FIELD OF THE INVENTION

This invention relates to a novel class of cyclic oligomers which incorporate cyclic structures within the oligomer. More particularly, the invention relates to cyclic oligomers in which 2-hydroxy-1,3-propylene moieties alternate with moieties of a 1,6-diaza [4.4] spirodilactam or, optionally, moieties of di(oxyphenyl) compound.

BACKGROUND OF THE INVENTION

The term "phenoxy resin" is a generic term used to describe the amorphous, high molecular weight poly(-hydroxyether) derived illustratively from reaction of diphenols and epichorohydrin or from the reaction of diphenols and diglycidyl ethers of diphenols. The resins are tough, high modulus thermoplastic materials of established commercial utility. For example, a commercial phenoxy resin marketed by Union Carbide as "UCAR" ® Resin is produced from epichlorohydrin and 2,2-di(4-hydroxypropane). The product of the reaction of 2,2-di(4-hydroxyphenyl)propane and its corresponding diglycidyl ether is a second example of a commercial phenoxy resin. Such resins have utility in applications such as molded articles, films and packaging materials, coatings and adhesives but have not been extensively used as engineering thermoplastics because of a typically relatively low glass transition temperature.

When higher glass transition temperatures are desired in many thermoplastic polymers, it is generally beneficial to include within the polymeric structure one or more types of cyclic moiety. The reaction product of epichlorohydrin and a spirobiindol is disclosed in U.S. Pat. No. 4,672,102 wherein the product is said to have a high heat distortion temperature. A second type of phenoxy resin containing cyclic structures is broadly disclosed by Wang, U.S. Pat. No. 4,889,907, where the phenoxy resin contains moieties of a 1,6-diaza [4.4] spirodilactam and moieties of 2,2-di(hydroxyphenyl)-propane. It would be of advantage to provide related cyclic phenoxy resin oligomers containing moieties of a 2-hydroxy-1,3-propylene alternating with other cyclic moieties.

SUMMARY OF THE INVENTION

The present invention provides a novel class of cyclic spirodilactam polyhydroxy polyether oligomers having moieties of 2-hydroxy-1,3-propylene alternating in a cyclic oligomer chain with moieties of a 1,6-diaza [4.4] spirodilactam and, optionally, a 2,2-di(hydroxyphenyl) compound.

DESCRIPTION OF THE INVENTION

The novel cyclic polyhydroxy polyether oligomers of the invention are characterized by the presence of 2-hydroxy-1,3-propylene moieties, i.e., —CH$_2$CHOH—CH$_2$— moieties, alternating within a cyclic oligomeric structure with moieties derived from 1,6-diaza [4.4] spirodilactam and, optionally, di(hydroxyphenyl) compound. Such oligomers are produced by reaction of an epihalohydrin, particularly epichlorohydrin, with a hydroxyaryl-substituted 1,6-diaza [4.4] spirodilactam and, optionally, a di(hydroxyphenyl) compound in the presence of base.

The spirodilactam moieties which are present in the cyclic oligomers of the invention are derived from a 1,6-diazaspiro[4.4]nonane-2,7-dione compound which is substituted on each spiro ring nitrogen atom with a hydroxyaryl containing substituent. One class of such spirodilactams has up to 60 carbon atoms and is represented by the formula

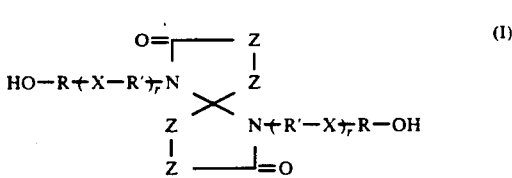

wherein Z independently is >C(Z')$_2$ in which Z' independently is hydrogen, lower alkyl of up to 4 carbon atoms inclusive, preferably methyl, halo, preferably the lower halogens fluoro, chloro or bromo, or aryl of up to 10 carbon atoms inclusive, preferably phenyl, or Z is such that two adjacent Z groups taken together form a ring system Z" of from 1 to 2 rings, each ring having from 5 to 7 ring atoms up to two of which are heteroatoms selected from nitrogen, oxygen or sulfur with the remainder of the ring atoms being carbon atoms, there being up to 15 carbon atoms inclusive in each Z", two of which connect the two spiro ring carbon atoms connected by the adjacent Z groups. In formula I, R independently is an aromatic group of up to 15 carbon atoms and up to 2 aromatic rings, inclusive, R' independently is R or an aliphatic group of up to 10 carbon atoms inclusive, X independently is a direct valence bond or X is alkylene of up to 8 carbon atoms inclusive, oxy, thio, sulfonyl, carbonyl, dioxyphenylene, 2,2-di(oxyphenyl)-propane, di(oxyphenyl) sulfone and diosydiphenylene, and r independently is 0 or 1. Each of R and R' is hydrocarbyl containing only atoms of hydrogen and carbon or is substituted hydrocarbyl containing additional atoms in the form of inert, monovalent carbon atom substituents such as halo, preferably the middle halogens chloro or bromo.

Spirodilactams of a variety of structures are therefore suitably employed as a source of the spirodilactam moieties in the cyclic oligomer of the invention. In the embodiment wherein the Z moieties of the compound of formula I are not a part of a fused ring and are therefore acyclic, i.e., Z is >C(Z')$_2$, the hydroxyaryl-substituted spirodilactams are illustrated by 1,6-di(4-hydroxyphenyl)-1,6-diazaspiro[4.4]nonane-2,7-dione, 1,6-di(3-hydroxy-4-chlorophenyl)-1,6-diazaspiro[4.4]nonane-2,7-dione, 1,6-di[4-(3-hydroxybenzoylphenyl)-3,8-dimethyl-1,6-diazaspiro[4.4]nonane-2,7-dione, 1,6-di(4-hydroxyphenyl)-3,3,4,4,8,8,9,9-octamethyl-1,6-diazaspiro[4.4]nonane-2,7-dione, 1,6-di[4-(4-hydroxybiphenyl)]-3,8-dimethyl-1,6-diazaspiro[4.4]nonane-2,7-dione, 1,6-di[2-(4-hydroxyphenyl)propyl]-1,6-diazaspiro[4.4]nonane-2,7-dione, 1,6-di[4-(4-hydroxyphenylisopropyl)phenyl]-1,6-diazaspiro[4.4]nonane-2,7-dione and 1,6-di(3-hydroxyphenyl)-3,4,8,9-tetrafluoro-1,6-diazaspiro[4.4]nonane-2,7-dione. In the embodiment where adjacent Z groups of each spiro ring form a cyclic structure fused to the spiro ring, i.e., adjacent Z groups are Z", illustrative spirodilactams include 1,6-di(4-hydroxyphenyl)-3,4,8,9-dibenzo-1,6-diazaspiro[4.4]nonane-2,7-dione, 1,6-di[4-(4-hydroxyphenyloxy)- phenyl)-3,4,8,9-di(pyrido)-1,6-diazaspiro[4.4]nonane-2,7-dione, and 1,6-di[4-(4-hydroxyphenylthio)phenyl]-3,4,8,9-cyclopentano-1,6-diazaspiro4.4]nonane-2,7-dione. Also suitable are those spirodilactams wherein one spiro ring has a fused cyclic substituent and the other spiro ring is free of fused cyclic substituent, e.g., 1,6-di(4-hydroxyphenyl)-3,4-benzo-methyl-1,6-diazaspiro[4.4]nonane-2,7-dione and 1,6-di[1-(4-hydroxynaphthyl)]-3,4-cyclohexano-1,6-diazaspiro[4.4]nonane-2,7-dione.

In general, the compounds of the above formula I wherein both R and R' are aromatic groups and hydrocarbyl are preferred, especially such compounds wherein each r is zero. The class of 1,6-di(hydroxyphenyl) spirodilactams is particularly preferred, especially the 1,6-di(4-hydroxyphenyl) spirodilactams. Within the spirodilactam portion of the molecule, spirodilactams are preferred wherein each spiro ring is free of fused ring substituents, i.e., each Z is >C(Z')$_2$, or both spiro rings have fused ring substituents, i.e., adjacent Z groups of each spiro ring are Z". The compound 1,6-di(4-hydroxyphenyl)-1,6-diazaspiro[4.4]nonane-2,7-dione is a particularly preferred member of the former class and 1,6-di(4-hydroxyphenyl)-3,4,8,9-dibenzo-1,6-diazaspiro[4.4]nonane-2,7-dione is a particularly preferred member of the latter class.

The hydroxyaryl-substituted spirodilactams of the above formula I are compounds which are described and claimed in Wang, U.S. Pat. No. 4,939,251 as is the method of their production This patent is incorporated herein by reference and describes production of the spirodilactams by the reaction of at least one hydroxy-containing primary amino compound and a spirodilactam precursor.

In terms of the spirodilactam of formula I, the hydroxy-containing primary amino compound is represented by the formula

HO—R—X—R'$_r$NH$_2$     (II)

wherein R, R', X and r have the previously stated meanings. The spirodilactam precursor is a 4-oxoheptanedioic acid compound or a 1,6-dioxaspiro-[4.4]nonane-2,7-dione. In terms of the spirodilactam of formula I, the 4-oxoheptanedioic acid compounds are represented by the formula

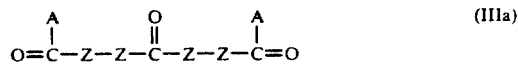

$$\underset{O=C-Z-Z-C-Z-Z-C=O}{\overset{A \quad\quad O \quad\quad A}{|\quad\quad\;||\quad\quad\;|}} \quad (IIIa)$$

wherein Z has the previously stated meaning and A independently is hydroxy, lower alkoxy of up to 4 carbon atoms inclusive or halo, preferably middle halo. The spirodilactone spirodilactam precursor, in terms of the spirodilactam of formula I, is represented by the formula

(IIIb)

wherein Z has the previously stated meaning.

The acyclic 4-oxoheptanedioic acid compounds are known compounds or are produced by known methods but certain of the compounds of formula IIIa, i.e., those compounds wherein A is alkoxy, are conveniently produced by the process of U.S. Pat. No. 4,800,231, incorporated herein by reference. Interconversion of the acids, esters and acid halides of formula IIIa is by conventional methods. The production of 4-oxoheptanedioic acid compounds which contain fused cyclic substituents is by the process of Cava et al, J. Am. Chem. Soc., 77, 6022 (1955). The spirodilactones of formula IIIb are produced by the process of Pariza et al, Synthetic Communications, Vol. 13(3), pp. 243-254 (1983) or by the process of Conover et al, U.S. Pat. No. 1,999,181.

The hydroxy-containing primary amino compound and the spirodilactam precursor react in a molar ratio of 2:1 although in practice molar reactant ratios from about 8:1 to about 1:1.5 are satisfactory. Reactant ratios that are substantially stoichiometric, i.e., 1:1, are preferred. Reaction is conducted in liquid phase solution in an inert reaction diluent such as an amide, e.g., N,N'-dimethylformamide, N,N-dimethylacetamide or N-methyl-2-pyrrolidone, or an ether such as tetrahydrofuran, dioxane or diethylene glycol diethyl ether. Reaction takes place under reaction conditions at an elevated temperature, typically from about 80° C. to about 250° C. The reaction pressure is sufficient to maintain the reaction mixture in a liquid phase. Such pressures are up to about 20 atmospheres. Subsequent to reaction, the spirodilactam product of formula I is recoverable from the product mixture by conventional methods such as solvent removal, precipitation and chromatographic separation. Recovery of the spirodilactam is not required, however, and particularly in those cases where substantially stoichiometric quantities of the reactants were employed the spirodilactam may be reacted further in situ without isolation or recovery.

The cyclic oligomers of the invention are produced by contacting the spirodilactam and, if present, the di(hydroxy) compound, and epihalohydrin, particularly epichlorohydrin, in the presence of base. The di(hydroxyphenyl) compound has up to 30 carbon atoms and, up to 2 aromatic rings, inclusive. Such compounds are illustrated by dihydroxybenzenes such as hydroquinone and resorcinol, dihydroxynaphthalenes such as 2,7-dihydroxynaphthalene and 1,5-dihydroxynaphthalene as well as by the class of di(hydroxyphenyl) compounds of the formula

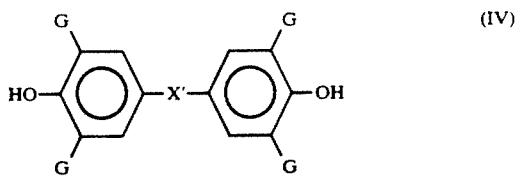

(IV)

wherein G independently is hydrogen, lower alkyl or middle halo, and X' is a direct valence bond or X' is alkylene of up to 8 carbon atoms inclusive, oxy, thio, sulfonyl, carbonyl. Illustrative of such compounds of formula IV are 2,2-di(hydroxyphenyl)propane, 2,2-di(4-hydroxy-3-methylphenyl)propane, 2,2-di(4-hydroxy-3-chlorophenyl)methane, di(4 hydroxy-3,5-dibromophenyl) ketone, 4-hydroxyphenyl 4-hydroxy-3-bromophenyl ether and 4-hydroxy-3,5-dibromophenyl 4-hydroxy-3-methylphenyl sulfone. The preferred X' group is 2,2-propylene and the preferred compound of formula IV is 2,2-di(4-hydroxyphenyl)propane, also known as bisphenol A or BPA.

The process of producing the novel oligomers of the invention preferably comprises the contacting of the hydroxyaryl-containing spirodilactam and epichlorohydrin in the optional presence of di(hydroxyphenyl) compound and in the presence of base. In one embodiment, the hydroxy-containing reactant or reactants and epichlorohydrin are contacted and base is subsequently added to complete the reaction. In an alternate embodiment, base is provided to the initial reaction mixture and oligomerization is conducted in one process step. Suitable bases for the reaction include organic bases such as amines but preferred bases are alkali metal compounds, particularly sodium or potassium hydroxide, carbonate or bicarbonate.

In the oligomerization process, di(hydroxyphenyl) compound is not required but quantities of di(hydroxyphenyl) compound up to about 9 moles per mole of hydroxy-aryl-containing spirodilactam are suitable. When present, quantities of di(hydroxyphenyl) compound from about 0.5 mole to about 2 moles per mole of hydroxyaryl-substituted spirodilactam are preferred. The epichlorohydrin is provided in a quantity from about 0.5 moles to about 2 moles per mole of total hydroxy-containing reactant. Quantities of epichlorohydrin that are substantially stoichiometric, i.e., about 1 mole of epichlorohydrin for each mole of total hydroxy-containing reactant are preferred.

The oligomerization is conducted under oligomerization conditions and typically in the presence of an inert polar diluent such as an amide or ether as described above. It is frequently useful to also have water present to facilitate the dissolution of inorganic reactants and by-products. Oligomerization conditions typically include a temperature of from about 50° C. to about 15° C. and frequently the reflux temperature of the reaction mixture is employed and is suitable. The reaction pressure is sufficient to maintain the reaction mixture in liquid phase. Such pressures are generally up to 20 atmospheres but pressures from about 0.8 atmospheres to about 5 atmospheres are preferred. During oligomerization, the contact of the reactants is facilitated by some means of agitation such as shaking, stirring or refluxing. Subsequent to reaction the oligomer product is recovered by conventional methods such as precipitation or selective extraction following the acidification of the product mixture and removal of any unreacted starting material and any higher polymer that formed during oligomerization. It is often useful to separate any aqueous phase that is present and to precipitate from the organic layer any polymer of realtively high molecular weight as by addition of a non-solvent. The oligomer product of the process is then recovered as by solvent removal or chromatographic separation.

The oligomer product is a co-oligomer or is a ter-oligomer depending upon whether di(hydroxyphenyl) compound was provided to the reaction mixture. Within the oligomer, moieties of 2-hydroxy-1,3-propylene alternate with moieties of 1,6-di(oxyphenyl)-1,6-diazaspiro[4.4]nonane-2,7-dione and, optionally, di(oxyphenyl) compound moieties. In terms of the preferred reactant structures, when the oligomer is a co-oligomer having only 2-hydroxypropylene moieties and oxyaryl-substituted spirodilactam moieties, the cyclic oligomer contains first segments represented by the formula

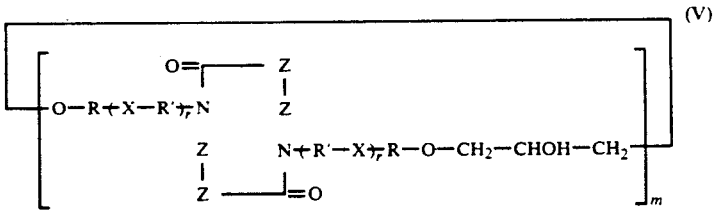

wherein R, R', r, X and Z have the previously stated meanings and m is an average number from 2 to 20 inclusive. In the modification where the cyclic oligomer product is a cyclic ter-oligomer, the product additionally incorporates second segments represented by the formula

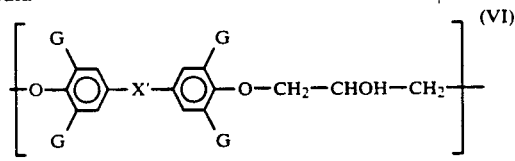

wherein G has the previously stated siginifcance, which second segments are found randomly throughout the oligomer chain. Within a ter-oligomer, the ratio of second segments to first segments is up to about 9:1 but preferably is from about 2:1 to about 1:2. It will be appreciated that the oligomer product comprises a mixture of oligomeric species of differing molecular weight so that m represents the average of first segments per oligomer molecule. The oligomer will have relatively little linear oligomer present, if any. In general, no more than about 5% by weight of linear oligomer is present. Higher molecular weight material may also be present, but generally in a quantity of no more than 10% by weight, preferably no more than about 5%.

The nomenclature of the oligomer products is not easily determined because of the complexity thereof. However, a representative cooligomer contains alternating moieties of 2-hydroxypropylene and moieties of 1,6-di(4-oxyphenyl)-1,6-diazaspiro[4.4]nonane-2,7-dione. A representative ter-oligomer additionally contains moieties of 2,2-di(4-oxyphenyl)propane found randomly throughout the oligomer in a relationship such that the 2-hydroxy-1,3-propylene moieties alternate with oxyphenyl-containing moieties. The identity of other cyclic oligomer products will be apparent from consideration of the above formulas for the reactants and the oligomer products. Of particular interest are the co-oligomers and ter-oligomers having molecular weights from about 500 to about 5,000, preferably from about 750 to about 3000.

The cyclic oligomers are useful in many of the applications conventionally associated with phenoxy resins such as in the production of films and shaped articles. The cyclic oligomers are also useful as intermediates in the production of linear, high molecular weight spirodilactambased polyhydroxy polyethers such as those described in U.S. Pat. No. 4,889,907. These higher molecular weight materials are produced by ether-ether interchange including the contacting of the cyclic oligomers of the invention with conventional nucleophilic initiators for ring-opening polymerization such as sodium sulfate, sodium thiophenoxide and pyridine in the melt or in solution in a polar, inert solvent such as N,N-dimethylacetamide.

The invention is further illustrated by the following Illustrative Embodiment which should not be regarded as limiting.

ILLUSTRATIVE EMBODIMENT

A mixture of 22.83 g (0.1 mole) of 2,2-di(4-hydroxyphenyl)propane, 18.5 g (0.2 mole) of epichlorohydrin, 33.8 g (0.1 mole) of 1,6-di(4-hydroxyphenyl)-1,6-diazaspiro[4.4]nonane-2,7-dione, 8.2 g (0.2 mole) of sodium hydroxide, 32 g of water and 51.2 g of ethanol was stirred for 16 hours at room temperature. At the end of 16 hours, an additional 1.2 g (0.03 mole) of sodium hydroxide in 4.8 g of water was added and the mixture was heated to reflux at about 80° C. After 30 minutes at reflux, 6 ml of tetrahydrofuran was added and after 60 minutes at reflux an additional 6 ml of tetrahydrofuran was added. The resulting mixture was refluxed for an additional 4 hours and 1.8 g of phenol in 12 ml of tetrahydrofuran was added. After an additional 2 hours at reflux, heating was discontinued and the aqueous layer was removed by decantation. To the organic layer was added 150 ml of N-methyl-2-pyrrolidone and the polymer-containing solution was coagulated with water. A white polymer precipitated and was recovered by filtration. The polymer was found to have a molecular weight of 85,000 as determined by gel permeation chromatography. The filtrate was stripped to provide oligomers containing 2-hydroxy-1,3-propylene moieties alternating with moieties of 1,6-di(4-oxyphenyl)-1,6-diazaspiro[4.4]nonane-2,7-dione moieties and 2,2-di(4-oxyphenyl)propane moieties. Field desorption mass spectroscopy of the oligomers showed masses of 678, 788, 962, 1072, 1182, 1246, 1466 and 1530 corresponding to differing combinations of 1,6-di(4-oxyphenyl)-1,6-diazaspiro[4.4]nonane-2,7-dione and 2,2-di(4-oxyphenyl)propane moieties alternating with 2-hydroxy-1,3-propylene moieties and, in several instances, only spirodilactam moieties alternating with 2-hydroxy-1,3-propylene moieties.

What is claimed is:

1. A polyhydroxy polyether cyclic oligomer wherein (a) moieties of 2-hydroxy-1,3-propylene alternate with (b) moieties of 1,6-di(oxyphenyl) 1,6-diaza spirodilactam and optionally, a di(hydroxyphenyl) compound.

2. The oligomer of claim 1 having a first segment of the formula

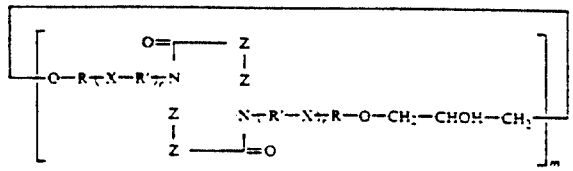

and, optionally, a second segment of the formula wherein R independently is an aromatic group of up to 15 carbon atoms and up to 2 aromatic rings, inclusive,

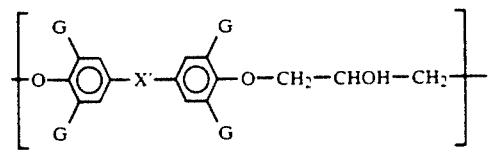

R' is R or an aliphatic group of up to 10 carbon atoms inclusive, X independently is a direct valence bond or X is alkylene of up to 8 carbon atoms inclusive, oxy, thio, sulfonyl, carbonyl, dioxyphenylene, 2,2-di(oxyphenyl)-propane, di(oxyphenyl) sulfone or dioxydiphenylene, Z independently is $>C(Z')_2$ in which Z' independently is hydrogen, lower alkyl, fluoro, chloro or bromo or phenyl or Z is such that two adjacent Z moieties taken together form a ring system Z" of from 1 to 2 rings, each ring having from 5 to 7 atoms, up to 2 of which are heteroatoms selected from nitrogen, oxygen or sulfur with the remainder of the ring atoms being carbon atoms, there being up to 15 carbon atoms in each Z", two of which form a bridge between the carbon atoms connected by the adjacent Z moieties, X' is a direct valence bond or X' is alkylene of up to 8 carbon atoms inclusive, oxy, thio, sulfonyl or carbonyl, G independently is hydrogen, chloro or bromo or lower alkyl, r is 0 or 1 and m is an average number from 2 to 20 inclusive.

3. The oligomer of claim 2 which is a co-oligomer of repeating first segment.

4. The oligomer of claim 3 wherein R' is R.

5. The oligomer of claim 4 wherein r is zero.

6. The oligomer of claim 5 wherein Z is $>C(Z')_2$.

7. The oligomer of claim 6 wherein Z' is hydrogen or methyl.

8. The oligomer of claim 7 wherein R is phenylene.

9. The oligomer of claim 8 wherein Z' is hydrogen and R is 4-phenylene.

10. The oligomer of claim 5 wherein adjacent Z moieties are Z".

11. The oligomer of claim 10 wherein R is phenylene.

12. The oligomer of claim 11 wherein Z" is benzo.

13. The oligomer of claim 2 which is a ter-oligomer of the first and the second segments.

14. The oligomer of claim 13 wherein the ratio of the second segment to the first segment is from about 2:1 to about 1:2.

15. The oligomer of claim 14 wherein G is chloro or bromo.

16. The oligomer of claim 14 wherein G is bromo.

17. The oligomer of claim 14 wherein G is hydrogen.

18. The oligomer of claim 17 wherein r is zero.

19. The oligomer of claim 18 wherein X' is 2,2-propylene.

20. The oligomer of claim 19 wherein Z is $>C(Z')_2$.

21. The oligomer of claim 20 wherein Z' is hydrogen or methyl.

22. The oligomer of claim 21 wherein R is phenylene.

23. The oligomer of claim 22 wherein Z' is hydrogen and R is 4-phenylene.

24. The oligomer of claim 19 wherein adjacent Z moieties are Z".

25. The oligomer of claim 24 wherein R is 4-phenylene.

* * * * *